US008097270B2

(12) United States Patent
Ketelson et al.

(10) Patent No.: US 8,097,270 B2
(45) Date of Patent: *Jan. 17, 2012

(54) USE OF NANOPARTICLES AS CARRIERS FOR BIOCIDES IN OPHTHALMIC COMPOSITIONS (75) Inventors: Howard Allen Ketelson, Fort Worth, TX (US); Nissanke L. Dassanayake, Arlington, TX (US); Thomas Christopher Carey, Fort Worth, TX (US); David L. Meadows, Fort Worth, TX (US)

(73) Assignee: Novartis AG, Basel (CH)

( * ) Notice: Subject to any disclaimer, the term of this patent is extended or adjusted under 35 U.S.C. 154(b) by 1835 days.

This patent is subject to a terminal disclaimer.

(21) Appl. No.: 10/494,711

(22) PCT Filed: Dec. 20, 2002

(86) PCT No.: PCT/US02/41246
§ 371 (c)(1),
(2), (4) Date: May 6, 2004

(87) PCT Pub. No.: WO03/059193
PCT Pub. Date: Jul. 24, 2003

(65) Prior Publication Data
US 2004/0241206 A1 Dec. 2, 2004

Related U.S. Application Data (60) Provisional application No. 60/342,779, filed on Dec. 21, 2001.

(51) Int. Cl.
A61K 9/00 (2006.01)
A61K 9/14 (2006.01)

(52) U.S. Cl. .................................. 424/429; 424/489

(58) Field of Classification Search ................ 424/429, 424/489
See application file for complete search history.

(56) References Cited

U.S. PATENT DOCUMENTS

| 3,884,826 A * | 5/1975 | Phares et al. ............... 510/112 |
| 4,127,423 A | 11/1978 | Rankin |
| 4,271,143 A | 6/1981 | Schoenwald et al. |
| 4,365,030 A | 12/1982 | Oswald et al. |
| 4,374,745 A | 2/1983 | Sibley et al. |
| 4,394,179 A | 7/1983 | Ellis et al. |
| 4,804,539 A | 2/1989 | Guo et al. |
| 4,891,043 A | 1/1990 | Zeimer et al. |
| 4,923,699 A | 5/1990 | Kaufman |
| 5,037,647 A | 8/1991 | Chowhan et al. |
| 5,139,782 A | 8/1992 | Jung |
| 5,185,152 A | 2/1993 | Peyman |
| 5,403,598 A | 4/1995 | Beck et al. |
| 5,585,108 A | 12/1996 | Ruddy et al. |
| 5,654,262 A | 8/1997 | Desai et al. |
| 5,674,504 A | 10/1997 | Kauffmann |
| 5,741,817 A | 4/1998 | Chowhan et al. |
| 5,811,580 A | 9/1998 | Rhubright |
| 5,858,346 A | 1/1999 | Vehige et al. |
| 6,015,816 A | 1/2000 | Kostyniak et al. |
| 6,106,798 A * | 8/2000 | Kambe et al. ............ 423/594.17 |
| 6,143,799 A | 11/2000 | Chowhan et al. |
| 6,177,480 B1 | 1/2001 | Tsuzuki et al. |
| 6,180,093 B1 | 1/2001 | De et al. |
| 6,309,658 B1 * | 10/2001 | Xia et al. ..................... 424/405 |
| 6,319,464 B1 | 11/2001 | Asgharian |
| 6,403,609 B1 | 6/2002 | Asgharian |

FOREIGN PATENT DOCUMENTS

| EP | 1 008 340 | 6/2000 |
| EP | 0 947 203 | 2/2003 |
| JP | 9285529 | 11/1997 |
| WO | WO 88/05073 | 7/1988 |
| WO | WO 97/31709 | 9/1997 |
| WO | WO 99/32158 | 7/1999 |
| WO | WO 00/46147 | 8/2000 |
| WO | WO 03/011351 | 2/2003 |
| WO | 03059194 | 7/2003 |
| WO | 03059263 | 7/2003 |

OTHER PUBLICATIONS

BioSante; *BioSante Pharmaceuticals Announces Positive Insulin Pre-Clinical Trial Results*, www.biosantepharma.com; Nov. 5, 2001; p. 1.

BioSante; *CAP (Calcium Phosphate Nanoparticles A Novel Vaccine Adjuvant and Delivery System*; www.biosantepharma.com; p. 1, 2001.

BioSante; *BioSante Pharmaceuticals, Inc. Announces Positive Pre-Clinical IntraOcular Trial Results*; www.biospace.com; Jan. 7, 2002; p. 1-3.

Kreuter, J. "Nanoparticles" *Collonial Drug Delivery Systems*, edited by Jork Kreuter, Marcel Dekker, New York, (USA), Chapter 5, p. 219-342 (1994).

Grandolini, et al.; *Intercalation Compounds of Hydrotalcite-like Anionic Clays with Anti-inflammatory Argents—I. Intercalation and in vitro Release of Ibuprofen*; International Journal of Pharmaceutics; vol. 220; pp. 23-32; 2001.

Plaizier-Vercammen; *Rheological Properties of Laponite XLG, A Synthetic Purified Hectorite*; Pharmazie; vol. 47; p. 856-861; 1992.

Tiffany; *Viscoelastic Properties of Human Tears and Polymer Solutions*; Lacrimal Gland, Tear Film and Dry Eye Syndromes; Plenum Press, NY; p. 267-270; 1994.

(Continued)

*Primary Examiner* — Robert A Wax
*Assistant Examiner* — Aradhana Sasan
(74) *Attorney, Agent, or Firm* — Michael D. Rein (57) ABSTRACT The use of nanoparticles of inorganic materials (e.g., synthetic smectite clays) in ophthalmic compositions is described. The nanoparticles are utilized as biologically inert carriers or depots for biocides. The nanoparticles are particularly useful in preventing or reducing the uptake of biocides from ophthalmic compositions by contact lenses, when the compositions are applied to the lenses.

18 Claims, 2 Drawing Sheets

OTHER PUBLICATIONS

Calvo; *Comparative in Vitro Evaluation of Several Colloidal Systems, Nanoparticles, Nanocapsules, and Nanoemulsions, as Ocular Drug Carriers*; Journal of Pharmaceuticals Sciences; vol. 85; No. 5; pp. 530-536; 1996.

Zimmer; *Microspheres and Nanoparticles Used in Ocular Delivery Systems*; Advances Drug Delivery Reviews; vol. 16; pp. 61-73; 1995.

Gieseking; *The Mechanism of Cation Exchange in the Montmorillonite-Beidellite-Nontronite Type of Clay Materials*; Soil Science; vol. 47; p. 1-14; 1939.

*Contact Lenses that Dispense Prescription Drugs*; American Chemical Society; Public Release; Mar. 23, 2003; p. 1.

*Contact Lenses Used to Deliver Eye Drugs*; R&D Digest; Medical Devicelink; www.devicelind,com; May, 2003; p. 1-2.

Gulsen, et al. *A Novel Ophtalmic Drug Delivery Vehicle: Dispersion of Nanoparticles in Soft Contact Lenses*; American Chemical Society Symposium; $225^{th}$ ACS National Meeting; New Orleans, LA; Mar. 2003; p. 1.

*Clay Delivers DNA for Gene Therapy*; C&EN, Nov. 20, 2000, p. 41.

\* cited by examiner

Figure 1

Lens Uptake Seen With AL8496 (4 ppm)/Laponite® XLS Formulations

Lens Uptake Seen With AL8496 (6 ppm)/Laponite® XLS Formulations

Relationship of Surface Tension and Lens Uptake to Nanoparticle/Biocide Ratio

◆ = Surface Tension
■ = Lens Uptake

USE OF NANOPARTICLES AS CARRIERS FOR BIOCIDES IN OPHTHALMIC COMPOSITIONS

This application claims priority from International Patent Application Serial No. PCT/US02/41246 filed on Dec. 20, 2002, and United States Provisional Application Ser. No. 60/342,779, filed on Dec. 21, 2001.

BACKGROUND OF THE INVENTION

The present invention is directed to the field of ophthalmic pharmaceutical products, particularly products that may be applied directly to contact lenses. Products that are applied to contact lenses to clean, disinfect, enhance comfort, or otherwise treat the lenses are commonly referred to as "contact lens care products" or "CLC products".

The invention is particularly directed to the provision of CLC products and other types of ophthalmic formulations containing one or more chemical agents to prevent contamination of the formulations by bacteria, fungi or other microbes. Such agents are referred to herein as "antimicrobial preservatives". The invention is also directed to CLC products that contain one or more chemical agents to kill bacteria, fungi and other microorganisms that may accumulate on contact lenses when worn and handled by humans. Such agents are referred to herein as "disinfecting agents". Both the antimicrobial preservatives and the disinfecting agents may be referred to herein as "biocides".

The invention is broadly applicable to various types of ophthalmic pharmaceutical compositions, but it is particularly useful in the field of CLC products, especially products for treating soft contact lenses.

The terms "soft" and "hard" relative to contact lenses are generally associated with not only the relative hardness of the respective types of lenses, but also the type of polymeric material from which the lenses are formed. The term "soft" generally denotes a contact lens that is formed from a hydrophilic polymeric material, such as hydroxyethyl methacrylate or "HEMA", while the term "hard" generally denotes a lens that is formed from a hydrophobic polymeric material, such as polymethylmethacrylate or "PMMA". The surface chemistry and porosity of the hard and soft lenses is quite different. Soft lenses typically contain a large amount of water, are quite porous, and bear ionic charges on the exposed surfaces of the lenses, while hard lenses are considerably less porous and generally do not bear ionic surface charges.

The ionic surfaces and porous nature of soft contact lenses can lead to significant problems when the lenses come into contact with CLC products or other ophthalmic pharmaceutical compositions, due to chemical and/or physical interactions between the lenses and one or more components of the compositions. For example, cationic antimicrobial agents such as benzalkonium chloride, chlorhexidine, polyquaternium-1 and polyhexamethylene biguanide ("PHMB") are known to have a propensity for binding with the surfaces of soft contact lenses and/or to become entrained in the porous lens matrix. This binding or entrainment can lead to the accumulation of a high concentration of biocide on the surface of the lens and/or within the lens matrix. This accumulation of biocide can lead to ocular irritation. Accordingly, CLC products and other ophthalmic products that can be applied directly to contact lenses must be formulated so as to avoid chemical or physical interactions between components of the products and the lenses.

A prior approach to solving or avoiding the above-described problems is described in U.S. Pat. No. 5,037,647 (Chowhan, et al.). The Chowhan, et al. '647 patent describes the use of a complexing agent (i.e., citrate) to prevent or reduce binding between the cationic antimicrobial agent polyquaternium-1 and soft contact lenses. The invention of the Chowhan, et al. '647 patent has been employed in OPTI-FREE® Rinsing, Disinfection and Storage Solution, which has been marketed by Alcon Laboratories, Inc. (Fort Worth, Tex., USA) for several years.

The inventors of the Chowhan, et al. '647 patent found that citrate could be utilized to prevent binding between the lenses and polyquaternium-1 by forming a soluble, reversible complex between the negatively charged citrate ions and the positively charged polyquaternium-1 molecules. However, it was also found that the formation of this polyquaternium-1/citrate complex reduced the antimicrobial activity of polyquaternium-1. Thus, anionic complexing agents can be utilized to prevent uptake of a cationic antimicrobial agent by contact lenses, but the resulting complex may inhibit the activity of the antimicrobial agent.

The chemical structure and properties of the antimicrobial agent being utilized is another factor that must be considered. Some antimicrobial agents exhibit both ionic and hydrophobic interactions with contact lens materials. The use of an ionic complexing agent to prevent uptake of such antimicrobial agents does not address the uptake that results from hydrophobic interactions. Thus, there is a need for a means of preventing uptake that results from hydrophobic interactions between antimicrobial agents and contact lens materials.

Despite the success of the invention described in the Chowhan, et al. '647 patent, there is a need for additional methods of formulating CLC products and other ophthalmic products to prevent binding or entrainment of components of the products on or in soft contact lenses. There is particularly a need for formulation technology that minimizes or eliminates biocide uptake in contact lenses without compromising the preservative or antimicrobial disinfection efficacy of the formulation, as well as a need for technology that is applicable to both cationic antimicrobial agents and other types of antimicrobial agents. The present invention is directed towards fulfilling these needs.

The present invention addresses the above-discussed needs by utilizing inorganic nanoparticles to act as a carrier or depot for the biocides utilized in CLC products, such as contact lens disinfecting solutions, as well as other types of ophthalmic compositions.

Synthetic smectite particulates with nanoparticle size dimensions have been previously utilized in pharmaceutical compositions. However, the concept of utilizing nanoparticles as agents to prevent biocide uptake in contact lens care has not been disclosed or suggested in the prior art.

U.S. Pat. No. 6,177,480 B1 (Tsuzuki, et al.) describes the use of a synthetic clay material (i.e., Laponite™) as a wetting agent for contact lenses and to assist in the removal of lipid deposits from contact lenses by surfactants.

U.S. Pat. No. 6,015,816 (Kostyniak, et al.) describes an improved method using colloid particles, such as smectite clay minerals, as a substrate for ligands having antimicrobial activity, so as to control microbial growth on a material. The ligands are strongly bound to the substrate surface and in this way the leachability of the antimicrobial agent is limited.

The following publications may be referred to for further background regarding the use of synthetic clay materials in pharmaceutical compositions:

Plaizier-Vercammen, "Rheological properties of Laponite XLG, a synthetic purified hectorite" *Pharmazie*, volume 47, page 856 (1992);

Grandolini, et al. "Intercalation compounds of hydrotalcite-like anionic clays with anti-inflammatory agents: I. Intercalation and in vitro release of ibuprofen *International Journal of Pharmaceutics*, volume 220, numbers 1-2, pages 23-32 (Jun. 4, 2001); and U.S. Pat. No. 5,585,108 (Ruddy, et al.) "Formulations of Oral Gastrointestinal Therapeutic Agents in Combination with Pharmaceutically Acceptable Clays".

SUMMARY OF THE INVENTION

The present invention is based on the use of nanoparticle materials to facilitate the formulation of ophthalmic compositions, particularly antimicrobial compositions adapted for the disinfection of contact lenses. The nanoparticles function as a chemically inert carrier or depot for biocides and other components of ophthalmic compositions.

It has been found that at very low concentrations in aqueous solutions, the nanoparticles can be dispersed while retaining a clear solution, and that the particles are capable of functioning as carriers for the biocide molecules, as well as other components of ophthalmic pharmaceutical compositions. It has also been found that the particles can be utilized as carriers for biocides without compromising the microbiological activity of the biocides.

In a preferred embodiment of the present invention, the above-described synthetic inorganic nanoparticles are utilized to prevent the uptake of biocides by contact lenses, particularly soft contact lenses. Various biocides can be used as antimicrobial preservatives or disinfecting agents in CLC products. However, many of the more potent biocides can cause irritation to the cornea due to accumulation of the biocides in contact lenses. This problem is particularly prevalent with soft contact lenses formed from high water content materials referred to as "hydrogels".

The present invention is based on the discovery that a dispersion of nanoparticles in an appropriately buffered vehicle is effective in reducing or preventing the uptake of biocides by contact lenses. The nanoparticles are believed to act as carriers for the biocide molecules. By using this approach, the uptake of biocides by contact lenses is minimized without compromising the microbiological activity of the biocides.

The invention therefore provides for safer contact lens maintenance and less irritating solutions. Furthermore, due to the minute size of the nanoparticles, the solutions of the present invention remain clear and non-blurry, which is very important for ophthalmic compositions, particularly compositions utilized to treat contact lenses.

DETAILED DESCRIPTION OF THE INVENTION

The nanoparticles utilized in the present invention are formed from inorganic materials. The particles have colloidal dimensions, a large surface area and a high ion exchange capacity. The particles are generally referred to hereinafter as "inorganic nanoparticles". The use of synthetic inorganic nanoparticles is preferred.

The nanoparticles used in the present invention preferably have particle dimensions less than 100 nanometers ("nm"), but greater than 1 nm, with a standard deviation of the distribution of less than 10%. The morphology of the nanoparticles is not limited to being spherical; plate-like, cubic, ellipsoid or other particle shapes are also useful. The particles have surface areas ranging from 30-1000 square meters/gram ("$m^2$/g"), and have an overall negative surface charge at a pH in the range of 6.0-7.8. The particles display Newtonian viscosity behavior in the concentration ranges described herein.

The inorganic nanoparticles may also be surface modified depending on the application and stability requirements. Different types of nanoparticles may be combined to optimize the formulation properties.

The inorganic nanoparticles utilized in the present invention are preferably formed from clays that swell in aqueous solutions. These types of clays are referred to herein as being "hydrous". The use of nanoparticles of synthetic hydrous clays is preferred due to the commercial availability, purity, and well-defined chemical composition and physical properties of these materials. In addition, the synthetic clay nanoparticles are easier to formulate and can form colorless and transparent gels more readily than inorganic nanoparticles formed from naturally occurring clays.

Synthetic inorganic nanoparticles that are particularly useful include a synthetic smectite clay that is commercially available under the trademark Laponite® (Southern Clay Products, Gonzales, Tex., USA). Laponite® is a layered hydrous magnesium silicate prepared from simple silicates. The following publication may be referred to for further details concerning the physical properties and functions of Laponite®: "Laponite Technical Bulletin "Laponite-synthetic layered silicate—its chemistry, structure and relationship to natural clays" L204/01 g. Another synthetic magnesium aluminum silicate material is also commercially available under the trademark OPTIGEL® SH (Sud-Chemie, Louisville, Ky.).

Inorganic nanoparticles formed from naturally occurring hydrous clays may also be utilized, either in combination with a synthetic clay or alone. Examples of suitable naturally occurring clays include aliettite, beidellite, bentonite, hectorite, kaolinite, magadite, montmorillonite, nontronite, saponite, sauconite, stevensite and volkonskoite.

The following publications may be referred to for further details regarding the physical properties of various types of clay nanoparticles and the use of these materials as ion-exchange materials, viscosity modifiers and film forming agents:

Gieseking, J. E., "Mechanism of Cation Exchange in the Mont-Morillonite-Beidellite-Nontronite Type of Clay Minerals", *Soil Science*, volume 47, pages 1-14 (1939);

Theng, B. K. G., "Formation and Properties of Clay-Polymer Complexes", Elsevier, Amsterdam, (1979); and H. van Olphen, "Clay Colloid Chemistry", Krieger Publishing Company, Florida., Second Edition (1991).

Examples of other inorganic nanoparticle materials that may be utilized instead of or as in combination with the clay nanoparticles described above include zeolites, silica, aluminum oxide, cerium oxide, titanium oxide and zinc oxide. Nanometer sized silica particles, such as those supplied by Nalco (e.g., Nalco® 115 and 1140) and EKA Chemicals (NYACOL® grades), are readily available. Mineral oxide nanoparticles based on other metals are also commercially available. For example, mineral oxides (e.g., aluminum oxide, cerium oxide, titanium oxide and zinc oxide) having well defined nano-dimensions are available from Nanophase Technologies (Romeoville, Ill., USA) under the trade name "NanoTek®".

As indicated above, it has been discovered that the above-described inorganic nanoparticles are capable of functioning as carriers for biocides in ophthalmic compositions. Biocides are typically utilized in ophthalmic compositions to prevent contamination of the compositions by microbes, such as bacteria and fungi. The biocides utilized for this purpose are generally referred to as "antimicrobial preservatives".

The present invention is applicable to the use of nanoparticles as carriers for antimicrobial preservatives in various types of ophthalmic compositions, such as pharmaceutical compositions for treating glaucoma or other ocular maladies, artificial tear compositions, ophthalmic decongestants or astringents, and so on. However, the invention is particularly directed to the use of nanoparticles in products utilized to treat contact lenses, which are referred to herein as "CLC products".

It has been found that the inorganic nanoparticles described above are capable of acting as carriers or depots for biocides in CLC products or other ophthalmic compositions without inhibiting or otherwise interfering with the antimicrobial activity of biocides contained in those compositions. More importantly, it has been found that when the compositions of the present invention are applied to contact lenses, the inorganic nanoparticles are very effective in preventing the uptake of biocides from the compositions by the lenses. This finding is particularly important for compositions that remain in contact with lenses for extended periods, such as contact lens disinfecting solutions, which are typically used to disinfect contact lenses by soaking the lenses in small volumes of the solutions for a few hours or more.

The concentration of the nanoparticles utilized in specific ophthalmic formulations will primarily depend on the antimicrobial agent selected and the concentration of the antimicrobial agent being utilized. The identification of an ideal concentration of nanoparticles for a specific formulation can be determined by means of routine experimentation, conducted in accordance with the specifications and considerations described herein.

The concentration of biocide in solution is directly dependent on the concentration of nanoparticles in that solution. If the concentration of nanoparticles is too high, the antimicrobial activity of the biocide will be significantly impaired. Conversely, if the concentration of nanoparticles is too low, uptake of the biocide by contact lenses will not be prevented. Identification of the ideal concentration of nanoparticles for a specific formulation can therefore be determined by testing a series of formulations wherein the concentrations of the biocide and the nanoparticles are adjusted and the formulations are evaluated relative to both antimicrobial activity level and uptake of the biocide by contact lenses. The ideal concentration of nanoparticles is one at which the formulation maintains adequate antimicrobial activity levels with little or no uptake of the biocide by contact lenses. This concentration is referred to herein as "an effective amount".

The proper ratio of the concentration of nanoparticles to biocide concentration can also be monitored by means of measuring the surface tension of the solutions. Many biocides, including the preferred biocides described herein, are surface active. Consequently, if the addition of nanoparticles to a solution results in an increase in the surface tension of the solution, this is a clear indication that a significant amount of the biocide has become bound to the inorganic nanoparticles.

The selection of an appropriate concentration of inorganic nanoparticles is further illustrated by the laboratory testing discussed in Example 1, below. The ideal concentrations selected as a result of such testing may vary significantly from formulation to formulation, based on the particular type of nanoparticles being utilized, the biocide involved, and other factors apparent to those skilled in the art, but the concentrations will generally fall within the range of 0.000001 to 0.1 weight/volume percent ("w/v %").

The invention is not limited relative to the types of biocides that may be utilized. The preferred biocides include: chlorhexidine, polyhexamethylene biguanide polymers ("PHMB"), polyquaternium-1, and the amino biguanides described in co-pending U.S. patent application Ser. No. 09/581,952 and corresponding International (PCT) Publication No. WO 99/32158, the entire contents of which are hereby incorporated in the present specification by reference. The use of surface-active biocides is preferred.

The preferred antimicrobial agents are polyquaternium-1 and amino biguanides of the type described in U.S. patent application Ser. No. 09/581,952 and corresponding International (PCT) Publication No. WO 99/32158. The most preferred amino biguanide is identified in U.S. patent application Ser. No. 09/581,952 and corresponding PCT publication as "Compound Number 1", and has the following structure:

This compound is referred to below by means of the code number "AL8496".

The ophthalmic compositions of the present invention will contain one or more ophthalmically acceptable biocides in an amount effective to prevent microbial contamination of the compositions, or in an amount effective to disinfect contact lenses by substantially reducing the number of viable microorganisms present on the lenses.

The levels of antimicrobial activity required to preserve ophthalmic compositions from microbial contamination or to disinfect contact lenses are well known to those skilled in the art, based both on personal experience and official, published standards, such as those set forth in the United States Pharmacopoeia ("USP") and similar publications in other countries, including the "stand alone" disinfection standard for contact lenses specified in ISO 14729:2001(E).

As indicated above, the preferred inorganic nanoparticles are synthetic smectite clays marketed under the trade name "Laponite®", and the preferred biocides are polyquaternium-1 and amino biguanides such as AL8496. Based on testing described herein, it has been determined that the optimum ratio of Laponite® to AL8496 for use in contact lens disinfecting solutions is 5:1 to 12:1, on a weight basis.

The ophthalmic compositions of the present invention will generally be formulated as sterile aqueous solutions. The compositions must be formulated so as to be compatible with ophthalmic tissues and contact lens materials. The compositions will generally have an osmolality of from about 200 to about 400 milliosmoles/kilogram water ("mOsm/kg") and a physiologically compatible pH.

The ophthalmic compositions of the present invention may contain various substances in addition to the above-described inorganic nanoparticles and biocides, such as surfactants, buffers and viscosity adjusting agents. The compositions may contain one or more components to enhance the antimicrobial activity of the compositions, such as: a borate/polyol complex (e.g., borate/sorbitol), as described in U.S. Pat. No. 6,143,799 (Chowhan, et al.); a low molecular weight amino alcohol (e.g., AMP_, as described in U.S. Pat. No. 6,319,464 (Asgharian); or a low molecular weight amino acid (e.g., glycine), as described in U.S. Pat. No. 5,741,817 (Chowhan, et al.). The entire contents of the above-referenced patents are hereby incorporated in the present specification by reference.

The ability of the above-described inorganic nanoparticles to reduce the uptake of biocides by contact lenses is demonstrated in the following examples.

EXAMPLE 1

In order to evaluate the ability of the nanoparticles to reduce the uptake of a biocide by contact lenses, a study was initiated using a cycle model regimen.

Nine formulations were evaluated in this study. The compositions of the formulations are set forth in Table 1, below. The formulations were prepared in 1 liter ("L") batches as follows. First, clay nanoparticles (Laponite® XLS) were dispersed in 600 milliliters ("mL") of purified water (room temperature) using a 3—blade Heidolph stirrer at 800 revolutions per minute ("rpm") for 30 minutes. After 30 minutes, the required amount of a 10% stock solution of the Tetronic® (poloxamine) surfactant was added to the clay dispersion. The dispersion containing the surfactant was mixed at 400 rpm for a further 30 minutes and set aside for autoclaving. The autoclaving was performed at 121 degrees centigrade ("° C.") for 30-35 minutes and then allowed to cool to room temperature. A pre-sterilized magnetic stirrer was added to the vessel containing the autoclaved dispersion and this was mixed while a 350 mL concentrate of the buffer vehicle was prepared. The buffer vehicle was added dropwise to the stirring dispersion. After adjusting the pH, the biocide (i.e., "AL8496") was added at the appropriate concentration. Enough purified water was added in the final step to make up a 100% batch scale formulation.

ACCUVUE® brand contact lenses were used in the study. The lenses were treated as follows. Two lenses were placed in 10 mL of the test solution. The lenses were subjected to 10 cycles, twice per day. The lenses were extracted with 1% trifluoroacetic acid/acetonitrile (10 mL) and sonication was performed for 2 hours at 40° C. The amount of biocide uptake by the lenses was calculated as micrograms per lens ("µg/lens"). The results of these calculations are shown in Table 1, below:

These values correspond to 89% and 80% reductions in the uptake of AL8496, respectively.

A similar trend was observed using the Laponite® XLS concentration of $5.0 \times 10^{-3}$ (w/v %). For example, the 9319-64K and 9319-64L formulations and at AL8496 concentrations of 4 ppm and 6 ppm showed reduced uptake values of 20.4 µg/lens and 37.5 µg/lens, respectively, using the cycle model. These values correspond to 76% and 74% reductions in the uptake of AL8496, respectively. Table 1 also shows data at pH 7.0, whereby the uptake of AL8496 was also reduced using the Laponite® dispersions.

Figure 1:
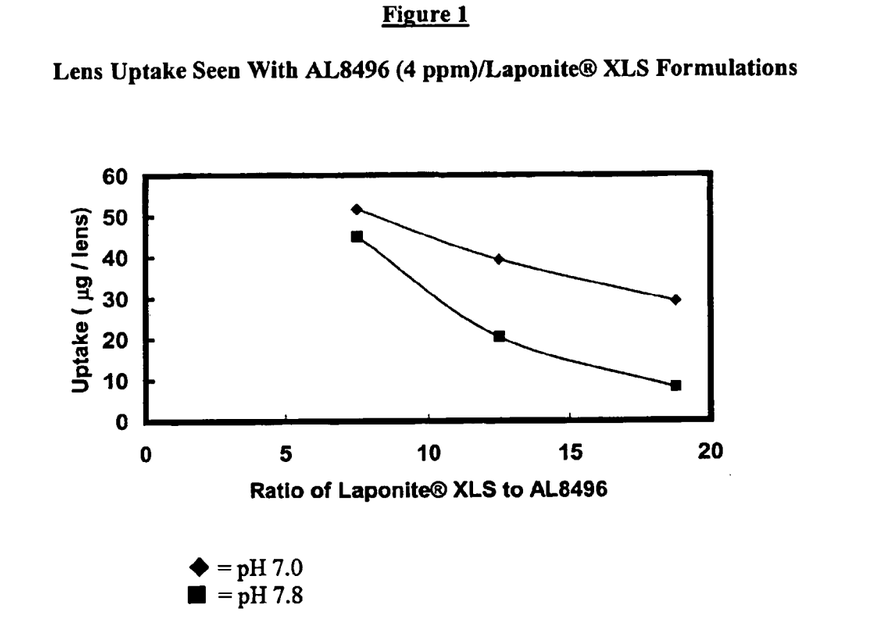
FIG. 1 is a graph showing the reduction of lens uptake of a particular biocide (AL8496 at a concentration of 4 ppm) as a function of the nanoparticle to biocide ratio.
Figure 2:
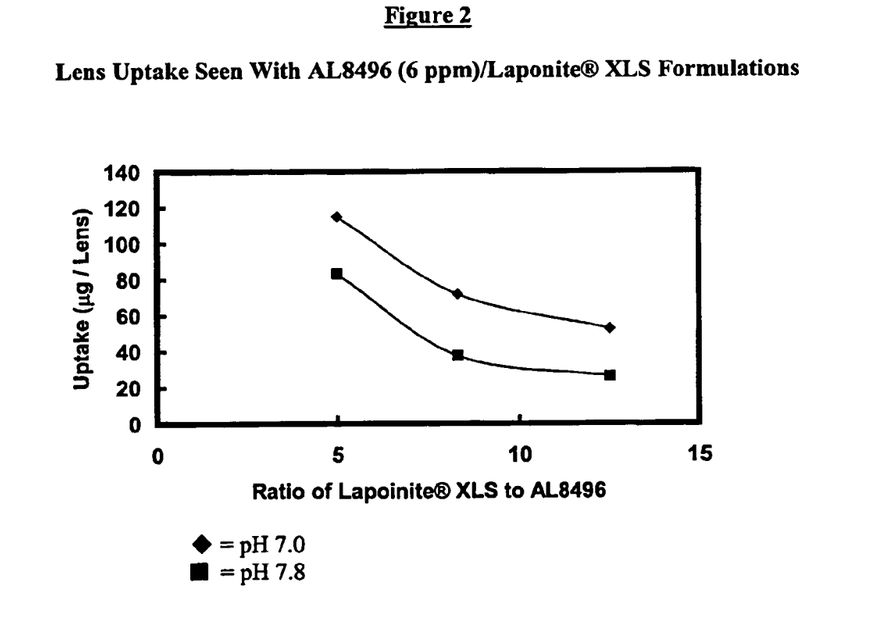
FIG. 2 is a graph showing the reduction of lens uptake of a particular biocide (AL8496 at a concentration of 6 ppm) as a function of the nanoparticle to biocide ratio.

The results set forth in Table 1 above are also shown in the graphs of FIGS. 1 and 2, which are plots of lens uptake values versus the ratio of Laponite® XLS to AL8496. FIGS. 1 and 2 graphically illustrate the influence of Laponite® XLS on the uptake of AL8496 at concentrations of 4 ppm and 6 ppm, respectively.

FIGS. 1 and 2 clearly illustrate the effect of the concentration of the clay nanoparticles on uptake. Specifically, as the concentration of clay nanoparticles was decreased, the uptake values increased.

As explained above, the selection of an ideal concentration of clay nanoparticles for a particular biocide formulation can be determined by means of routine experimentation. The concentration of the clay nanoparticles must be at a level that is effective to either eliminate the uptake of the biocide completely or reduce the uptake of the biocide to an acceptable

TABLE 1

Lens Uptake and Antimicrobial Activity of Laponite ® XLS Formulations with AL8496

| Component | Concentration (% w/v) | | | | | | | | |
|---|---|---|---|---|---|---|---|---|---|
| | 9319-64E | 9319-64G | 9319-64H | 9319-64I | 9319-64K | 9319-64L | 9319-64M | 9319-64O | 9319-64P |
| Laponite ® XLS | $7.5 \times 10^{-3}$ | $7.5 \times 10^{-3}$ | $7.5 \times 10^{-3}$ | $5.0 \times 10^{-3}$ | $5.0 \times 10^{-3}$ | $5.0 \times 10^{-3}$ | | | |
| AL-8496A | 0.0004 | 0.0004 | 0.0006 | 0.0004 | 0.0004 | 0.0006 | 0.0004 | 0.0004 | 0.0006 |
| Sodium borate | 0.2 | 0.2 | 0.2 | 0.2 | 0.2 | 0.2 | 0.2 | 0.2 | 0.2 |
| Sodium citrate | 0.6 | 0.6 | 0.6 | 0.6 | 0.6 | 0.6 | 0.6 | 0.6 | 0.6 |
| Sorbitol | 0.4 | 0.4 | 0.4 | 0.4 | 0.4 | 0.4 | 0.4 | 0.4 | 0.4 |
| Tetronic ® 1304 | 0.1 | 0.1 | 0.1 | 0.1 | 0.1 | 0.1 | 0.1 | 0.1 | 0.1 |
| Propylene glycol | 1.0 | 1.0 | 1.0 | 1.0 | 1.0 | 1.0 | 1.0 | 1.0 | 1.0 |
| EDTA | 0.05 | 0.05 | 0.05 | 0.05 | 0.05 | 0.05 | 0.05 | 0.05 | 0.05 |
| pH | 7.0 | 7.8 | 7.8 | 7.0 | 7.8 | 7.8 | 7.0 | 7.8 | 7.8 |

| Microorganism | Time (hours) | $Log_{10}$ Reduction of Survivors | | | | | | | |
|---|---|---|---|---|---|---|---|---|---|
| | | 9319-64 E | 9319-64G | 9319-64H | 9319-64I | 9319-64K | 9319-64L | 9319-64M | 9319-64O | 9319-64P |
| C. albicans | 6 | 0.8 | 1.1 | 2.3 | 0.9 | 1.7 | 3.0 | 1.5 | 2.8 | 3.2 |
| | 24 | 2.5 | 4.4 | <u>6.0</u> | 2.7 | 5.0 | <u>6.0</u> | 3.6 | 4.1 | <u>6.0</u> |
| S. marcescens | 6 | 4.3 | 4.3 | 4.5 | 3.4 | 2.7 | 3.1 | 3.5 | 2.5 | 2.6 |
| | 24 | 4.4 | 4.4 | 3.6 | 3.9 | 3.3 | 4.2 | 5.1 | 3.3 | 6.1 |
| S. aureus | 6 | 3.1 | 4.1 | 4.6 | 3.3 | 4.1 | 4.5 | 5.2 | 4.0 | <u>5.9</u> |
| | 24 | 4.3 | <u>5.9</u>$^a$ | <u>5.9</u> | 4.9 | <u>5.9</u> | <u>5.9</u> | <u>5.9</u> | <u>5.9</u> | <u>5.9</u> |
| Uptake (cycle) µg/lens | | 29.1 | <u>8.1</u> | 26.1 | 39.3 | 20.4 | 37.5 | 85.5 | 66.3 | 105.3 |

*Underlined number indicates no survivors (<10 CFU/mL) recovered

The data in Table 1 show that the control solutions, which did not contain clay nanoparticles, exhibited very high biocide uptake levels. The uptake values for AL8496 in the control solutions (9319-64M, 9319-64O and 9319-64P) were determined to be 85 µg/lens, 66.3 µg/lens and 105.3 µg/lens, respectively using the cycle model. However, in the test dispersions containing low levels of clay nanoparticles, in accordance with the present invention, the uptake of AL8496 was significantly reduced.

For example, in the dispersions at pH 7.8 containing $7.5 \times 10^{-3}$ (w/v %) Laponite® XLS and either 4 ppm (9319-64G) or 6 ppm (9319-64H) of AL8496, the uptake values were determined to be 8.1 µg/lens and 26.1 µg/lens, respectively.

level. However, if the concentration of clay nanoparticles is too high, the particles will bind the biocide and reduce its antimicrobial activity.

Figure 3:
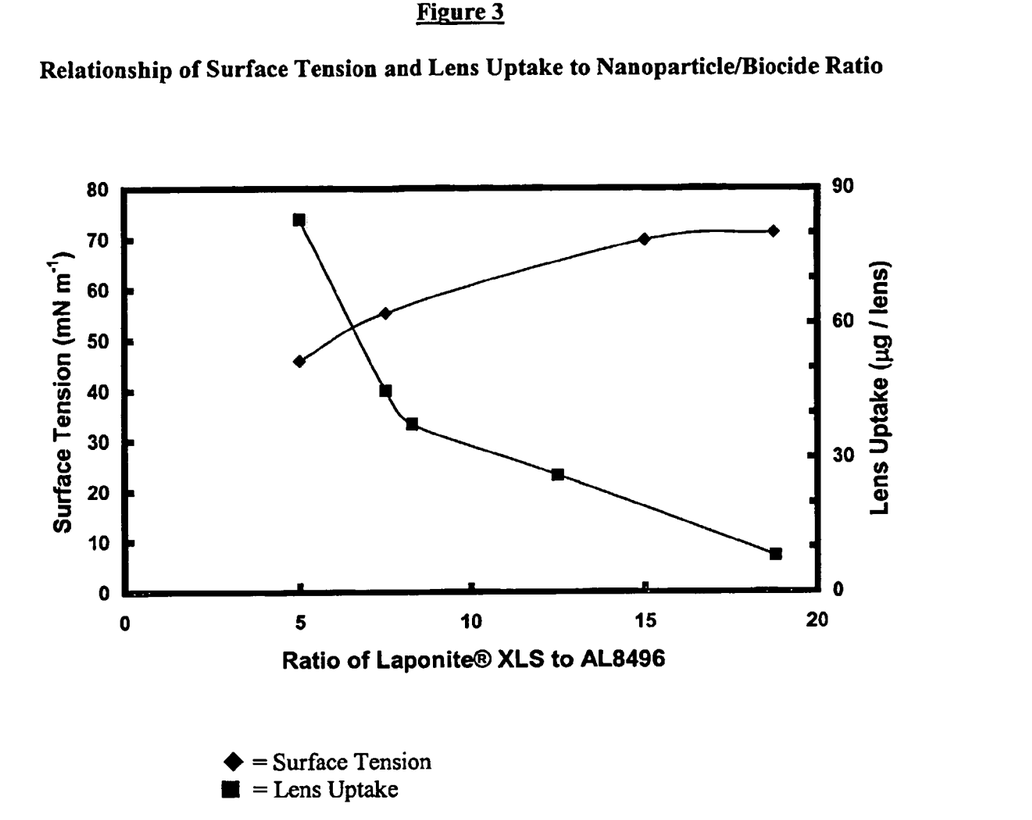
FIG. 3 is a graph showing surface tension and lens uptake as a function of the nanoparticle to biocide ratio.

One approach to determine the optimum concentration of Laponite® with AL8496 or other biocides is to determine the surface tension of Laponite® dispersions in the presence of the biocide. Higher surface tensions will generally correspond to lower levels of biocide in solution (i.e., the biocide will be bound to the surfaces of the clay particles and consequently will not be available to reduce the surface tension of water). Surface tension reduction will correspond to excess biocide available to the bulk solution that will result in lowering the surface tension of water. FIG. 3 shows a graph of two plots whereby the left y-axis corresponds to the surface tension of various Laponite® XLS dispersions with AL8496, whereas the right y-axis corresponds to the AL8496 lens uptake data in the presence of Laponite® XLS.

FIG. 3 shows that the surface tension increased as the Laponite® XLS to AL8496 ratio increased. This trend was expected, because the higher concentration of clay in solution for a particular biocide concentration would lead to a reduced concentration of biocide available in solution for antimicrobial activity. FIG. 3 also shows that the lens uptake decreased significantly with increasing Laponite® XLS to AL8496 ratios.

From a practical point of view, FIG. 3 shows that there is an optimum Laponite® XLS/AL8496 ratio where enough AL8496 will be available to meet disinfection criteria (without compromising the lens uptake). FIG. 3 shows that low levels of Laponite® type nanoparticles can be used in the presence of biocides to control uptake of the biocides by the lenses, and this control is directly related to the amount of biocide adsorbed on the clay particles.

Table 1 above shows the antimicrobial activity of Laponite® XLS formulations with AL8496 against 3 organisms (*C. albicans, S. marcescens, S. aureus*) at 6 and 24 hours.

The data in Table 1 at pH 7.8 shows that the two control formulations (without Laponite® XLS) at 4 ppm (9319-64O) and 6 ppm (9319-64P) display good antimicrobial activity for all three test organisms. The use of Laponite® in these formulations at both the 4 ppm and 6 ppm AL8496 concentrations showed similar if not enhanced antimicrobial activity (i.e., especially for *S. marcescens*). For example, formulations 9319-64H and 9319-64L met stand-alone disinfection criteria. The antimicrobial data set forth in Table 1 demonstrate that the formulations maintained efficacious levels of antimicrobial activity in the presence of low levels of clay nanoparticles (i.e., Laponite® XLS).

The use of a particular Laponite® XLS to AL8496 ratio is further illustrated in FIG. 3. For example, formulation 9319-64G has a ratio of 18.75 and according to FIG. 3 it has a high surface tension coupled with a very low uptake. Comparatively, formulation 9319-64H and 9319-64L have Laponite® XLS to AL8496 ratios of 12.5 and 8.3, respectively. As shown in FIG. 3, the surface tensions are lower for these formulations, which reflects the availability of AL8496 in solution. Although the lens uptake of AL8496 seen with formulations 9319-64H and 9319-64L is higher than the uptake seen with formulation 9319-64G, there is a compromise between the lens uptake levels and antimicrobial activity levels of the formulations, which can be controlled by varying the Laponite® and biocide concentrations.

EXAMPLE 2

The ability of the nanoparticles described above to reduce biocide uptake is not limited to amino biguanides such as AL8496. The discovery that nanoparticles can reduce biocide uptake is also applicable to other biocides, such as polyquaternium-1, chlorhexidine, alexidine, hexetidine, polyhexamethylene biguanide, benzalkonium chloride, alkyl amines and other anti-microbial agents used as preservatives or disinfecting agents in ophthalmic products.

To further illustrate the use of nanoparticles with other biocides, we have formulated Laponite® XLS with benzalkonium chloride ("BAC"), which is a well-known alkyl quaternary ammonium biocide. Table 2 below shows the lens uptake (using the cycle model described in Example 1) and antimicrobial efficacy of the Laponite® dispersions (using $7.5\times10^{-3}$ w/v %) containing BAC at concentrations varying from 50 ppm to 100 ppm.

TABLE 2

Antimicrobial Activity of Laponite ® XLS Formulations with BAC

| Component | | Concentration (% w/v) | | | | | |
|---|---|---|---|---|---|---|---|
| | | 9319-80B | 9319-80C | 9319-80D | 9319-80J | 9319-80K | 9319-80L |
| Laponite XLS[a] | | 0.0075 | 0.0075 | 0.0075 | | | |
| Benzalkonium chloride | | 0.005 | 0.007 | 0.01 | 0.005 | 0.007 | 0.01 |
| Tetronic 1304 | | 0.1 | 0.1 | 0.1 | 0.1 | 0.1 | 0.1 |
| Sorbitol | | 0.4 | 0.4 | 0.4 | 0.4 | 0.4 | 0.4 |
| Sodium borate | | 0.2 | 0.2 | 0.2 | 0.2 | 0.2 | 0.2 |
| Sodium citrate | | 0.6 | 0.6 | 0.6 | 0.6 | 0.6 | 0.6 |
| Propylene glycol | | 1.0 | 1.0 | 1.0 | 1.0 | 1.0 | 1.0 |
| EDTA | | 0.05 | 0.05 | 0.05 | 0.05 | 0.05 | 0.05 |
| pH | | 7.8 | 7.8 | 7.8 | 7.8 | 7.8 | 7.8 |
| Osmolality | | 217, 213 | 208, 211 | 201, 204 | 223, 220 | 209, 208 | 212, 209 |
| | | $Log_{10}$ Reduction of Survivors | | | | | |
| Microorganism | Time (hrs) | 9319-80B 01-716 | 9319-80C 01-717 | 9319-80D 01-718 | 9319-80J 01-722 | 9319-80K 01-723 | 9319-80L 01-724 |
| *C. albicans* | 6 | 0.0 | 0.0 | 0.5 | −0.2 | 0.6 | 1.3 |
| | 24 | 0.0 | 1.2 | 2.3 | 1.1 | 2.5 | 3.3 |
| *S. marcescens* | 6 | 1.5 | 3.2 | 4.1 | 3.6 | 3.3 | 5.5 |
| | 24 | 2.5 | 6.2[c] | 6.2 | 4.2 | 3.1 | 6.2 |
| *S. aureus* | 6 | −0.1 | 2.3 | 4.3 | 3.7 | 4.6 | 4.7 |
| | 24 | 1.3 | 6.0 | 6.0 | 6.0 | 6.0 | 6.0 |
| | | | 9204: 031(STS) | | | | |
| Uptake(Cycle) µg/Acuvue lens | | 10.8 | 22.8 | 44.4 | 28.2 | 56.4 | 83.4 |

[a]Lot 99/310

[b]Research Microbiology test article number

[c]Underlined number indicates no survivors (<10 CFU/mL) recovered

The uptake data in Table 2 show a similar trend to the lens uptake values obtained for the Laponite®/AL8496 formulations described in Example 1 above. The lens uptake data of formulations 9319-80B, 9319-80C and 9319-80D containing 50 ppm, 70 ppm and 100 ppm BAC in the presence of 7.5× $10^{-3}$ w/v % Laponite® XLS were determined to be 10.8 µg/lens, 22.8 µg/lens and 44.4 µg/lens, respectively. In contrast, the lens uptake data for BAC formulations in the absence of Laponite® were much higher. The formulations 9319-80J, 9319-80K and 9319-80L containing 50 ppm, 70 ppm and 100 ppm BAC were determined to have uptake values of 28.2 µg/lens, 56.4 µg/lens and 83.4 µg/lens, respectively, using the cycling model outlined in Example 1. These values are approximately two times greater than the values seen with the corresponding formulations containing Laponite® particles. Thus, the use of synthetic inorganic nanoparticles (i.e., Laponite®) in these formulations resulted in reductions of the uptake of BAC by approximately 50%.

The data in Table 2 also show the antimicrobial activity results. The control formulations (9319-80J, 9319-80K and 9319-80L) having BAC concentrations of 50 and 70 ppm showed negligible activity towards *C. albicans* at 6 hours, whereas at 100 ppm (9319-80L) a 1.3 log reduction was achieved. BAC is well known as a preservative and its efficacy towards fungi is not very high. Thus, the ability to obtain a reduction of greater than one log order with formulation 9319-80L against *C. albicans* was unexpected.

Formulations 9319-80C and 9319-80D showed negligible *C. albicans* activity at 6 hours. On the other hand, the antimicrobial results of the Laponite® formulations containing 70 and 100 ppm BAC showed excellent efficacy relative to the bacteria tested (*S. marcescens* and *S. aureus*), at both 6 and 24 hours.

The above-discussed data support the use of Laponite® with BAC to prepare effective antimicrobial formulations with reduced lens uptake.

EXAMPLE 3

The uptake of AL8496 with Laponite® using six different lenses was explored. The formulations are described in Table 3, below while the uptake data are shown in Table 4, below.

TABLE 3

AL8496 Formulations

| Formulation Chemical (% wt/% vol) | 9591-14A[1] | 9591-14B |
|---|---|---|
| AL8496 | 0.0006 | 0.0006 |
| Laponite ® XLG (lot 00/213) | 7.5 × $10^{-3}$ | — |
| Tetronic 1304 | 0.1 | 0.1 |
| Sorbitol | 0.4 | 0.4 |
| Sodium Borate | 0.2 | 0.2 |
| Sodium Citrate | 0.6 | 0.6 |
| Propylene Glycol | 1.0 | 1.0 |
| EDTA | 0.05 | 0.05 |
| Purified Water | QS | QS |
| pH | 7.8 | 7.8 |

TABLE 4

Uptake Data For Various Lens Types in the Presence of Laponite ® XLG/AL8496

| Lens Group | Lens/Components | Type of Polymer | 9591-14A, µg/Lens | 9591-14B, µg/Lens |
|---|---|---|---|---|
| I | CSI ® (Crofilcon A 38% $H_2O$) W/J | Non ionic | 7.2 | 42.8 |
| II | Soflens ™ 66 (alfafilicon A 66% $H_2O$) B&L | Non ionic | 7.8 | 40 |
| III | DuraSoft ® 2 (phemfilcon A 38% $H_2O$) W/J | Ionic | 30.4 | 108.4 |
| III | Pure Vision ™ (balafilcon, 36% $H_2O$) B&L | Ionic | 71.0 | 162 |
| IV | Surevue ® (etafilconA 58% $H_2O$) J/J | Ionic | 28.2 | 114 |
| IV | DuraSoft ® 3 (phemfilcon A 55% $H_2O$) W/J | Ionic | 47.6 | 147.2 |
| IV | Acuvue ® (etafilcon 58% $H_2O$)J/J | Ionic | 24.2 | 104 |

Laponite ® XLG at a concentration of 7.5 × $10^{-3}$ w/v % was used in combination with 6 ppm of AL8496 (9591-14A) and lens uptake with various lens types was evaluated using the cycle model described above. The uptake exhibited by formulation 9591-14A was compared to a control solution that did not contain Laponite ® (9591-14B).

The data in Table 4 above show that the lens uptake values obtained with formulation 9591-14A were significantly lower than those seen with the control solution (9591-14B) which did not contain Laponite®. The data presented in Table 4 show that the incorporation of Laponite® in biocide formulations to reduce uptake is not restricted to any particular lens type.

EXAMPLE 4

The uptake of AL8496 at both 2 ppm and 4 ppm by Acuvue II lenses after 2 cycles using nanosilica particles (Nyacol®) was explored. The compositions tested and corresponding uptake data are described in Table 5. The formulations were prepared in accordance with the procedures described in Example 1. The uptake procedures were the same as in Example 1.

TABLE 5

AL8496 Formulations and Uptake Data after 2 cycles using Nyacol ®

| Formulation Chemical (% wt. % vol.) | 9736-79A | 9736-79B | 9736-79C | 9736-79D | 9736-79E | 9736-79F |
|---|---|---|---|---|---|---|
| AL-8496A | 0.0002 | 0.0004 | 0.0002 | 0.0004 | 0.0002 | 0.0004 |
| Nyacol ® 1430 | — | — | 0.005 | 0.005 | 0.025 | 0.025 |
| Sodium Citrate | 0.6 | 0.6 | 0.6 | 0.6 | 0.6 | 0.6 |
| Propylene Glycol | 1.0 | 1.0 | 1.0 | 1.0 | 1.0 | 1.0 |
| Sorbitol | 0.4 | 0.4 | 0.4 | 0.4 | 0.4 | 0.4 |
| Tetronic 1304 | 0.05 | 0.05 | 0.05 | 0.05 | 0.05 | 0.05 |

TABLE 5-continued

AL8496 Formulations and Uptake Data after 2 cycles using Nyacol ®

| Formulation Chemical (% wt. % vol.) | 9736-79A | 9736-79B | 9736-79C | 9736-79D | 9736-79E | 9736-79F |
|---|---|---|---|---|---|---|
| EDTA | 0.05 | 0.05 | 0.05 | 0.05 | 0.05 | 0.05 |
| Sodium Borate | 0.2 | 0.2 | 0.2 | 0.2 | 0.2 | 0.2 |
| pH | 7.8 | 7.8 | 7.8 | 7.8 | 7.8 | 7.8 |
| Uptake (µg/lens) (2 cycles) | 9.4 | 16 | 5.8 | 8.2 | 3.0 | 6.0 |

The data in Table 5 above show that the lens uptake values obtained with the formulations containing the 2 ppm and 4 ppm of AL8496 were lower when Nyacol® 1430 was used. The control formulations (9736-79A and 9736-79B) had uptake values of 9.4 µg/lens and 16 µg/lens, respectively. A comparison of these uptake values with the formulations containing Nyacol® (9736-79C and 9736-79D) shows that reductions in uptake of approximately 40-50% were achieved. Thus, the data presented in Table 5 demonstrate that the incorporation of silica nanoparticles (Nyacol®) in AL8496 formulations reduces the uptake of biocide by contact lenses.

We claim:

1. A method of reducing the uptake of a biocide by a contact lens from an ophthalmic composition containing a surface-active biocide while maintaining antimicrobial effectiveness, which comprises including an amount of inorganic nanoparticles selected from the group consisting of hydrous clays, and silica, in the range from about 0.000001 to about 0.1 weight/volume percent in the composition, said composition having a pH in the range of 6.0 to 7.8, thereby reducing the uptake of the surface-active biocide by the contact lens.

2. An ophthalmic composition comprising a surface-active biocide and an amount of inorganic nanoparticles selected from the group consisting of hydrous clays, and silica, in the range from about 0.000001 to about 0.1 weight/volume percent, said composition having a pH in the range of 6.0 to 7.8, whereby the composition reduces biocide uptake into contact lenses while maintaining antimicrobial effectiveness.

3. A composition according to claim 2, wherein the composition is an aqueous solution utilized to disinfect contact lenses.

4. A composition according to claim 3, wherein the biocide is a biguanide.

5. A composition according to claim 4, wherein the biocide is an amino biguanide.

6. A composition according to claim 3, wherein the biocide is a quaternary ammonium compound.

7. A composition according to claim 6, wherein the quaternary ammonium compound is polyquaternium-1.

8. A method of using inorganic nanoparticles as a carrier or depot for a biocide in an ophthalmic pharmaceutical composition, said method comprising adding inorganic nanoparticles selected from the group consisting of hydrous clays, and silica, in the range from about 0.000001 to about 0.1 weight/volume percent in the composition, said composition having a pH in the range of 6.0 to 7.8, whereby the amount of inorganic nanoparticles is sufficient to prevent or reduce the uptake of the biocide by contact lenses while maintaining adequate antimicrobial activity levels to the ophthalmic pharmaceutical composition.

9. A method according to claim 1, wherein the uptake of biocide is reduced by from about 40% to about 89%.

10. The composition according to claim 2, wherein the pH is equal to or greater than about 7.0.

11. The method according to claim 8, wherein the amount of nanoparticle is selected to provide at least 40% reduction in uptake of biocide.

12. The method according to claim 8, wherein the ratio of the amount of nanoparticles in w/v % relative to the amount of biocide in w/v % is between 5 and 20.

13. The composition according to claim 2, wherein the surface-active biocide is a cationic biocide.

14. The composition according to claim 13, wherein the biocide is a quaternary ammonium compound.

15. The composition of claim 2, whereby the composition provides at least a 40% reduction in uptake of biocide relative to a composition without nanoparticles.

16. The composition of claim 2, wherein the composition is selected from the group consisting of pharmaceutical compositions, artificial tear compositions and ophthalmic decongestants or astringents.

17. The composition of claim 16, wherein the pharmaceutical composition is a composition for treating glaucoma.

18. The composition of claim 2, wherein the amount of inorganic nanoparticles is no greater than about 0.01 weight/volume percent.

* * * * *